(12) United States Patent
Tulleken

(10) Patent No.: US 8,734,436 B2
(45) Date of Patent: May 27, 2014

(54) LASER CATHETER FOR BYPASS SURGERY AND ASSEMBLY COMPRISING SAID CATHETER

(75) Inventor: Cornelis Antonius Franciscus Tulleken, Utrecht (NL)

(73) Assignee: AMJ bv (NL)

( * ) Notice: Subject to any disclaimer, the term of this patent is extended or adjusted under 35 U.S.C. 154(b) by 300 days.

(21) Appl. No.: 12/918,447

(22) PCT Filed: Feb. 21, 2008

(86) PCT No.: PCT/NL2008/050101
§ 371 (c)(1),
(2), (4) Date: Aug. 19, 2010

(87) PCT Pub. No.: WO2009/104949
PCT Pub. Date: Aug. 27, 2009

(65) Prior Publication Data
US 2010/0331793 A1     Dec. 30, 2010

(51) Int. Cl.
*A61M 25/00*     (2006.01)
*A61B 18/20*     (2006.01)

(52) U.S. Cl.
USPC ........ 606/15; 606/7; 606/13; 606/14; 606/16; 607/92

(58) Field of Classification Search
USPC .......................... 606/15, 13, 14, 16, 7; 607/92
See application file for complete search history.

(56) References Cited

U.S. PATENT DOCUMENTS

| | | | |
|---|---|---|---|
| 5,725,544 A * | 3/1998 | Rygaard | 606/167 |
| 5,964,750 A * | 10/1999 | Tulleken et al. | 606/15 |
| 6,395,016 B1 | 5/2002 | Oron et al. | |
| 6,626,920 B2 * | 9/2003 | Whayne | 606/153 |
| 2006/0009682 A1 * | 1/2006 | Nagasawa et al. | 600/171 |

FOREIGN PATENT DOCUMENTS

| | | |
|---|---|---|
| DE | 101 07 687 A1 | 9/2002 |
| EP | 0 411 496 A | 2/1991 |
| EP | 0 750 476 A | 1/1997 |
| WO | 95/24869 | 9/1995 |
| WO | WO-2009104949 A1 | 8/2009 |

OTHER PUBLICATIONS

Cornelis A.F. Tulleken, "End-to-Side Anastomosis of Small Vessels Using an ND:YAG Laser with a Hemispherical Contact Probe", 12589 Journal of Neurosurgery 76 Mar. 1992, Hanover, NH, US.
"European Application Serial No. 08712627.2, Amended Claims filed Nov. 8, 2010", 8 pgs.
"European Application Serial No. 08712627.2, Non Final Office Action dated Jul. 21, 2011", 4.

* cited by examiner

*Primary Examiner* — Jessica Stultz
*Assistant Examiner* — Michael Carter
(74) *Attorney, Agent, or Firm* — Schwegman, Lundberg & Woessner, P.A.

(57) ABSTRACT

The invention is directed to a laser catheter (1) for bypass surgery, wherein the distal part (2) of the catheter (1) is provided with: a tubular arrangement (3) of optical fibers (4) having distal ends (5) defining a ring-shaped light emergence surface (6) for emitting a tubular bundle of light beams in the distal direction (D) of the catheter (1); and a stop surface (7) extending around the tubular arrangement (3) of optical fibers (4) and facing in the distal direction (D), the stop surface (7) being arranged at a distance (A) proximally from the light emergence surface (6). The light emergence surface (6) slants at a slanting angle (α) in the range of [20°, 60°] with respect to the longitudinal axis (8) of the catheter (1). The invention further relates to an assembly comprising such a catheter.

15 Claims, 6 Drawing Sheets

LASER CATHETER FOR BYPASS SURGERY AND ASSEMBLY COMPRISING SAID CATHETER

CROSS-REFERENCE TO RELATED APPLICATIONS

This application is the National Stage of International Application No. PCT/NL2008/050101, filed Feb. 21, 2008, the contents of which is incorporated by reference herein.

FIELD OF THE INVENTION

The present invention relates to a laser catheter for bypass surgery, wherein the distal part of the catheter is provided with:
a tubular arrangement of optical fibres having distal ends defining a ring-shaped light emergence surface for emitting a tubular bundle of light beams in the distal direction of the catheter,
a stop surface extending around the tubular arrangement of optical fibres and facing in the distal direction, the stop surface being arranged at a distance proximally from the light emergence surface.

BACKGROUND OF THE INVENTION

Such a laser catheter for bypass surgery is known from EP 750,476. This document describes the use in the ELANA (Excimer Laser Assisted Non-occlusive Anastomosis) operating technique. This Elana technique was developed by neurosurgeon C. A. F. Tulleken. For the Elana technique, one requires an Elana catheter and an Elana ring, which are jointly called Elana Arteriotomy System.

The catheter disclosed in EP 750,476 is used for performing an ETS-anastomosis (ETS=End To Side) between a graft vessel and a target vessel. The graft is fixed with an end to the side of the target vessel, while the blood flow through the target vessel, also called recipient vessel, is not interrupted, i.e. blood continues to flow through the target vessel while performing the anastomosis. For this purpose, first the graft vessel is fixed to the target vessel and subsequently, after this fixation is established, the flow connection between the target vessel and graft vessel is made by removing the part of the wall of the target vessel which lies in front of the fixed end of the graft vessel. Said part of the wall of the target vessel is removed by means of an tubular arrangement of optical fibres emitting a tubular bundle of laser light beams originating from the fibres and a suction gripper provided inside the tubular arrangement of optical fibres. The tubular bundle of laser light beams burns a circle into the wall of the target vessel, resulting in a circular passage connecting the lumens of the graft vessel and target vessel. The circular wall part of the target vessel—i.e. the part lying inside said burned circle—is gripped by the suction gripper and removed together with the withdrawal of the catheter after the burning operation. The distal ends of the optical fibres of this known laser catheter define a circle extending in a plane essentially perpendicular to the longitudinal axis of the catheter. During use the laser catheter extends perpendicular to the target vessel, resulting in a perpendicular ETS-anastomosis with a circular passage between the graft vessel and target vessel. In order to ensure a complete cutting away of tissue along the said circle, the teaching is that the cutting laser light beams should impinge on the target vessel as perpendicular as possible. This in order to avoid scattering of the laser light beams by inter alia reflection effects, which would maker the cutting action less effective and less reliable. A perpendicular impinging from the laser light beams further keeps the required depth of tissue to be burned away as short as possible. For example, in case the laser beams impinge at about 45° on the wall of the target vessel, the depth of tissue to be burned away is about 40% more than in case the laser beams impinge perpendicular.

There are however also applications, for example in the field of cardiovascular surgery but also in the field of surgery of intracranial arteries, in which a slanting ETS-anastomosis is desired or required. In a slanting ETS-anastomosis define the graft vessel and target vessel an angle different from 90°, in general in the range of 30°-60°.

SUMMARY OF THE INVENTION

The object of the present invention is to provide a laser catheter for bypass surgery, which is suitable for use in a slanting ETS-anastomosis procedure.

According to the invention this object is achieved by providing a laser catheter for bypass surgery, wherein the distal part of the catheter is provided with:
a tubular arrangement of optical fibres having distal ends defining a ring-shaped light emergence surface for emitting a tubular bundle of light beams in the distal direction of the catheter,
a stop surface extending around the tubular arrangement of optical fibres and facing in the distal direction, the stop surface being arranged at a distance proximally from the light emergence surface;
characterized in that the light emergence surface slants at a slanting angle in the range of [20°, 60°]—i.e. from and including 20° up to and including 60°—with respect to the longitudinal axis of the catheter.

A catheter provided with such a slanting light emergence surface can and may not be rotated along its longitudinal axis during the cutting procedure. This could result in failure of the cutting procedure, if not in a disaster, because, in case the slanting light emitting surface would be in a position which is not parallel to the wall of the target vessel, not all the laser light beams will impinge on the wall of the target vessel but some or many of them will impinge on the wall of the graft vessel and thus would burn a—not intended—whole in the graft vessel. Further assuming, as is the case during the cutting procedure, the light emergence surface extends close and parallel to the wall surface of the target vessel, the light emergence surface would push the adjacent wall tissue of the target vessel away in case the light emergence surface would be rotated with respect to the longitudinal axis of the catheter. However, it appears that this adjacent wall tissue of the target vessel develops a reaction force counter acting the pushing away of this adjacent wall tissue—thus functioning as a resistance force—and that this reaction force—or resistance force—helps preventing inadvertent rotation of the catheter during the cutting procedure and is slightly tangible for the surgeon. Applicant also surprisingly found that, the laser light beams also perform their cutting action very well in case they impinge upon the wall of the target vessel under an angle of 60° or even 20° (instead of 90°, as is the case in the prior art device).

According to a further embodiment, said slanting angle is in the range of [40°, 50°], such as about 45°. In practise this appears to be a frequently occurring anastomosis angle.

According to another further embodiment, the tubular arrangement of optical fibres has, viewed in a cross-section transverse to the longitudinal axis of the catheter, a circular cross section, wherein, viewed perpendicular to the light emergence surface, the shape of the light emergence surface is elliptical. This ensures that the aperture created in the wall of the target vessel allows for a optimal flow characteristics of the blood flowing from the target vessel into the graft vessel or from the graft vessel into the target vessel.

According to still another further embodiment, the stop surface and light emergence surface are parallel to each other. The stop surface forms locally a radial bulge on the outer surface of the catheter. When the catheter is inserted into the graft vessel, this bulge will be visible as a bulge in the wall of the graft vessel or at least tangible with the fingers of the surgeon. Taking into account that the stop surface and light emergence surface are parallel to each other, this means that the surgeon can use the bulge as a reference for the orientation of the light emergence surface. This enables the surgeon to control or correct the orientation of the light emergence surface with respect to the wall of the target vessel.

In order to remove the flap of wall tissue left after burning away the ring of tissue, it is advantageous to provide the distal part of the catheter with a gripper for gripping tissue inside the tubular bundle of light beams. According to the invention, the gripper preferably comprises a hollow channel extending within the tubular arrangement of fibres and connectable to a vacuum source, wherein the distal end of the channel defines a suction mouth. In order to ensure a reliable cutting through of the wall tissue of the target vessel by the laser light beams as well as a firm gripping of the cut out part of the wall tissue, it is according to the invention advantageous to arrange the suction mouth at a distance proximally from the light emergence surface and so that it defines a suction surface parallel to the light emergence surface. The suction surface parallel to the light emergence surface ensures an easy gripping of the cut out part all over its surface.

According to a further aspect, the invention relates to an assembly for bypass surgery, comprising:
a laser catheter according to the invention; and
a ring member having dimensions adapted for, on the one hand, insertion of the distal end of the tubular arrangement of optical fibres through said ring member and for, on the other hand, preventing passage of the stop surface through said ring member.

Before connecting the graft vessel to the target vessel, the graft vessel will be prepared for the bypass procedure by inserting one end of the graft vessel through the ring member and folding back the end of the graft vessel over the ring member. Before using the laser catheter, this folded end of the graft vessel, enclosing the ring member, will be attached to the wall of the target vessel. Subsequently, when the laser catheter has been introduced into the graft vessel and the laser operation is performed, the ring member will prevent the laser catheter from advancing too far into the target vessel as soon as the stop surface comes to rest onto the ring member.

According to a further embodiment of the assembly according to the invention it is advantageous when the ring member has an axial height which is at least 1 mm, such as in the range of [1, 5] mm or preferably in the range of [1, 3] mm, when the ring member has two opposing axial end faces, and when the angle between at least one of said axial end faces and the axial direction of the ring member corresponds to said slanting angle. A ring member having a axial height of at least 1 mm, such as 1 to 3 mm (including both 1 and 3 mm), provides a tubular guide for the distal ends of the optical fibres. This tubular guide helps preventing tilting of the laser catheter with respect to the target vessel during the laser procedure. The angle of the end face of the ring member, which faces the target vessel, being equal to the slanting angle, assists in ensuring that the light emergence surface is kept parallel to the wall of the target vessel during the laser operation. Preferably, both the axial end faces of the ring member are mutually parallel. This provides that the resting surface for the stop surface lies all around the ring member at the same distance from the target vessel.

According to a further embodiment, the assembly according to the invention, further comprises a graft vessel having diameter dimensions allowing, on the one hand, passage of the laser catheter and, on the other hand, insertion through said ring member. According to the invention, this graft vessel can be an artificial vessel as well as a donor vessel obtained from an animal, the patient or another person. Preferably, one end of the graft vessel is inserted through said ring member and folded back over said ring member.

As will be clear, the present invention might be used in many medical fields, especially in the field of surgery of blood vessels. Specific examples of use of the invention are endovascular surgery, especially endovascular bypass surgery, and surgery of intracranial arteries. The present invention might be used with the so called Elana technique.

BRIEF DESCRIPTION OF THE DRAWINGS

Below, the present invention will be described further with reference to the schematic drawing. In this schematic drawing:

FIG. 7 shows a sequence of steps in a ETS-anastomosis procedure according to the invention, which FIG. 7 is subdivided into the FIGS. 7a, 7b, 7c and 7d.

DETAILED DESCRIPTION OF THE INVENTION

Figure 1:
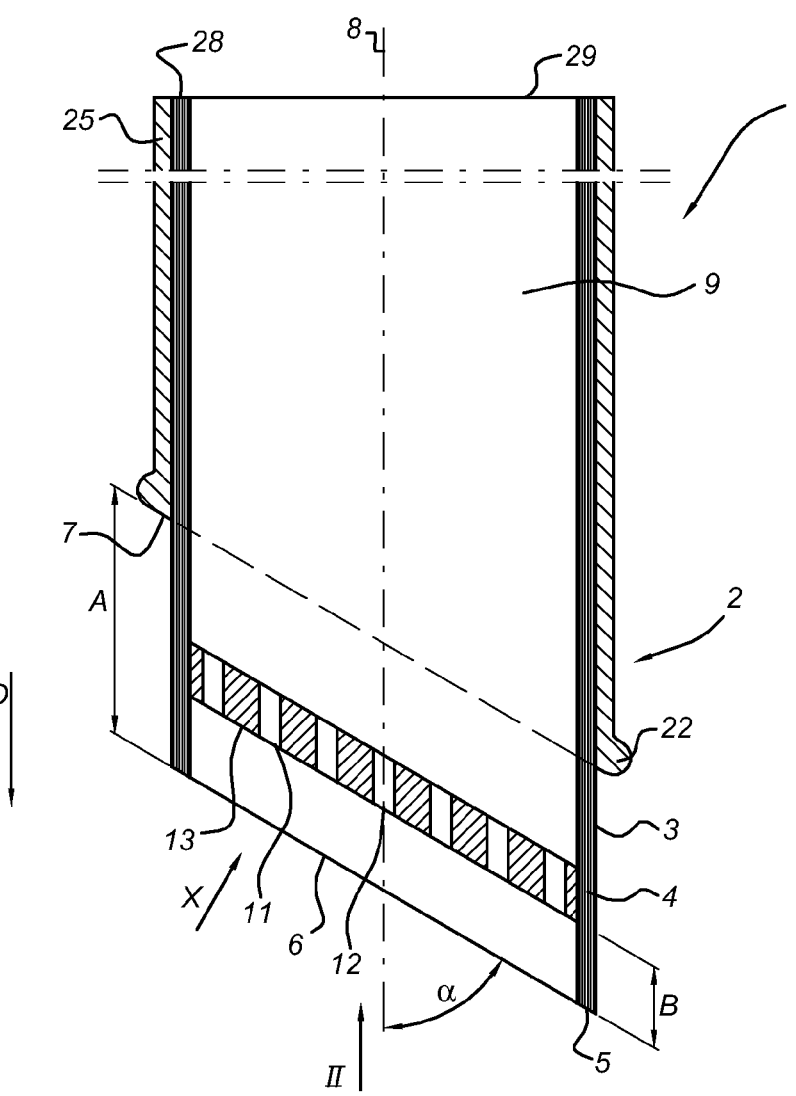
FIG. 1 shows a longitudinal cross section of a laser catheter according to the invention.
Figure 2:
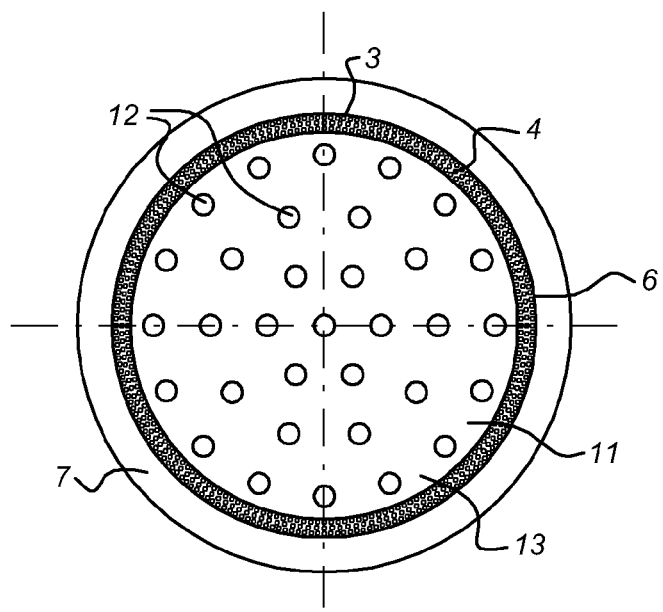
FIG. 2 shows an end view according to arrow II in FIG. 1.
Figure 3:
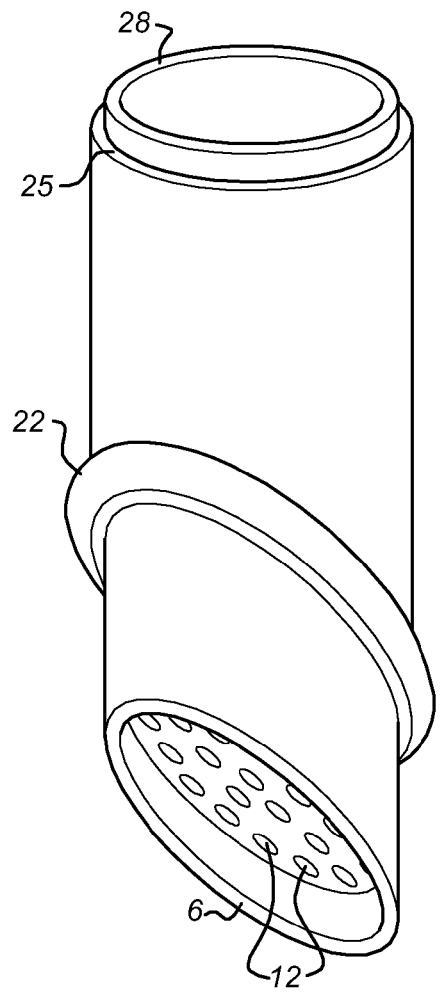
FIG. 3 shows a perspective view of the laser catheter of FIG. 1.

FIGS. 1, 2 and 3 show a laser catheter 1 according to the invention. The distal part 2 of the laser catheter 1 is provided with a tubular arrangement 3 of optical fibres 4. The optical fibres 4 have distal ends 5, which together define a ring-shaped light emergence surface 6. When a laser source is connected to the proximal ends 28 of the optical fibres 4, a laser light beam will emit from each of these distal ends 5 of the optical fibres 4. The distal ends of the optical fibres 4 extend parallel to the longitudinal axis 8 of the catheter, so that the emitted laser light beams will extend parallel to the longitudinal axis 8 in the distal direction indicated by arrow D. This results in a tubular bundle of laser light beams in the distal direction D of the catheter.

The laser catheter 1 further comprises a casing surrounding the tubular arrangement 3 of optical fibres. The tubular arrangement 4 encloses a channel 9. The proximal end 29 of the channel 9 can be connected to a vacuum source 10 (see FIG. 7c) in order to apply a suction force to the channel 9. The distal end of the channel 9 is provided with a plate, defining the suction surface 13 and provided with suction apertures 12. The distal end of the channel 9 thus forms a suction mouth 11, which acts as a gripper when vacuum is applied at the proximal end 29. The suction mouth is provided at a distance B proximally from the light emergence surface 6. This distance B will at least be about the thickness of the wall of the target vessel.

The distal end of the casing 25 is provided with a radial bulge 22. The distal side of the radial bulge 22 forms a stop surface 7. This stop surface lies proximally at a distance A from the light emergence surface 6. This distance A will at least be about the axial height H (see FIG. 4 and discussion further below) plus twice the wall thickness of the graft vessel (which follows from FIG. 7c discussed below) plus the wall thickness of the target vessel 21 (which also follows from FIG. 7c).

The laser catheter as described up to here with reference to FIGS. 1, 2 and 3 is essentially identical to the laser catheter disclosed in EP 750,476, i.e. the differences are not yet addressed.

The distal ends 5 of the optical fibres 4 lie closely packed together with the longitudinal walls of adjacent fibres against each other to form together a tubular arrangement 3 having a circular cross-section as can be seen in FIG. 2. The distal end faces of all the optical fibres 4 together define an essentially flat light emergence surface 6, which—according to this invention—slants at an angle $\alpha$ of between 30° to 60° (including both 30° and)60°, preferably about 45°, with respect to the longitudinal axis 8 of the catheter.

Due to the distal ends 5 of the optical fibres being closely packed, the bundle of light beams, which are emitted when a laser light source is connected, form an essentially continuous circular bundle which is capable of burning away a continuous ring of tissue from a target vessel. Rotation of this bundle of laser beams during laser operation for ensuring a complete cut through appears to be superfluous and can be dispensed with.

Due to the slanting light emergence surface, the light emergence surface can lie closely adjacent or against the wall of the target vessel during the laser operation—i.e. the application of the laser beams for burning away tissue—. This results in a very controlled application of the laser beams without the risk that those laser beams damage other surrounding tissue. This also results in that the laser beams, although they impinge under an angle $\alpha$ different from 90°, are still able to transfer sufficient energy to the tissue for burning it away.

In order to ensure a good gripping of the flap 14 (FIG. 7c)—i.e. the tissue part separated after burning away the ring of tissue—by the suction mouth 11, the suction surface 13 of the suction mouth extends parallel to the light emergence surface 6.

The bulge 22 with the stop surface 7 also extends parallel to the light emergence surface 6. For the stop function, a bulge and stop surface extending in a plane perpendicular to the longitudinal axis 8 would suffice. This bulge 22 however will provide the surgeon a visible or tangible reference for controlling the position of the light emergence surface with respect to the wall of the target vessel 21. It will be clear that the bulge 22 is preferably a bulge extending continuously around the catheter, but that, within the scope of the claims, it may also be a discontinuous bulge.

Referring to FIG. 3, it can be seen that the cross sectional shape—in a plane perpendicular to the longitudinal axis 8—of the catheter is circular, but that as such the light emergence surface 6, the stop surface 7, the bulge 22 and the gripper surface 13 have an oval shape (when viewed in a plane perpendicular to the viewing direction of arrow X in FIG. 1).

Figure 4:
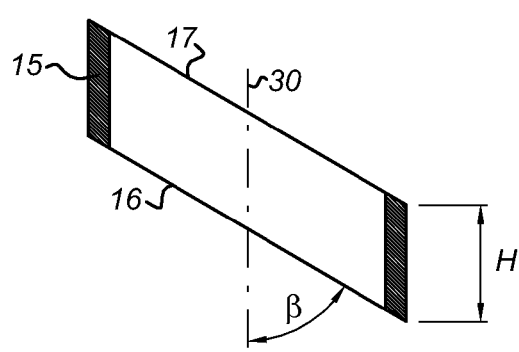
FIG. 4 shows a longitudinal cross section of a ring member belonging to an assembly according to the invention.
Figure 5:
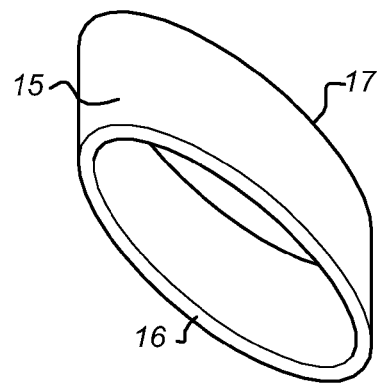
FIG. 5 shows a perspective view of the ring member of FIG. 4.

FIGS. 4 and 5 show a ring member 15, which together with the laser catheter of FIGS. 1-3 forms an assembly according to the invention. This ring member 15 is preferably made from a material which is inert for the human body, such as a metal alloy like a platinum-iridium alloy. This ring member 15 has a longitudinal axis 30 defining its axial direction. The ring member further has an axial height H of at least about 2-3 mm and two opposing axial end faces 16, 17. The axial height of at least about 2-3 mm provides a guiding sleeve for the distal end of the tubular arrangement 3 of fibres 4, which sleeve prevents tilting of the tubular arrangement 3 of fibres 4 with respect to the sleeve and consequently the target vessel. The two opposing axial end faces 16, 17 are preferably mutually parallel and have a slanting angle $\beta$ with respect to the longitudinal axis 30. The slanting angle $\beta$ is preferably identical to the angle $\alpha$ (see FIG. 1). The angle $\beta$ of the distal axial surface 16 determines in fact the angle $\gamma$ (see FIG. 7a) of the graft vessel 18 with respect to the target vessel 21, i.e. the slanting angle of the ETS-anastomosis. The proximal axial end face 17 being parallel to the distal axial end face 16, has the advantage that the slanting stop surface 7 can come to a firm rest along the entire circumference of the ring member 15.

Figure 6:
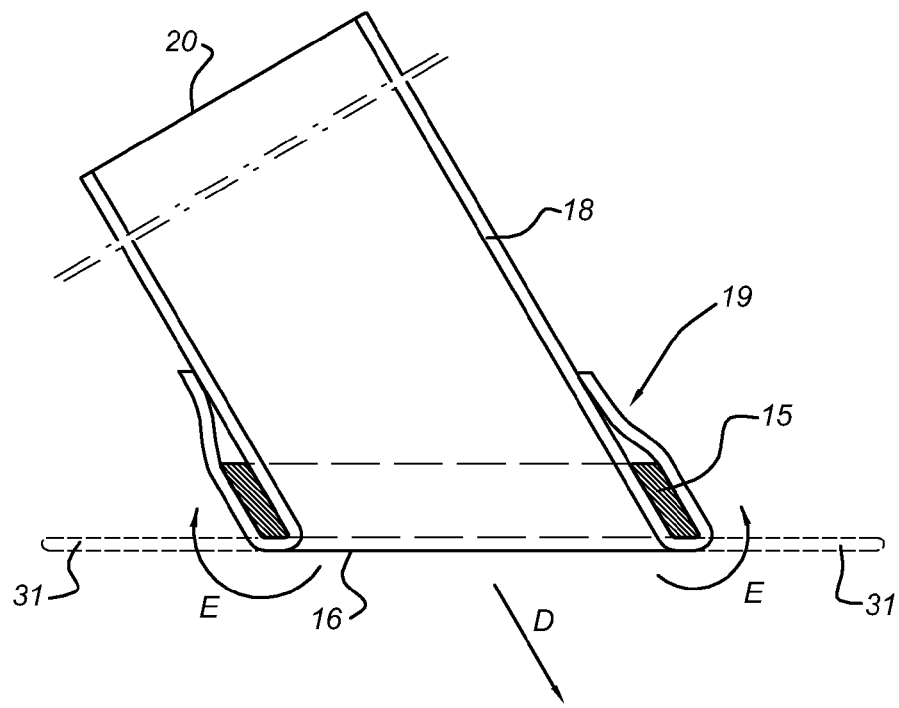
FIG. 6 shows a longitudinal cross section of a part of an assembly according to the invention.

FIG. 6 shows a configuration of ring member 15 and a graft vessel 18, which configuration together with the laser catheter of FIGS. 1-3 forms an assembly according to the invention. The graft vessel 18 can be an artificial vessel or donor vessel originating from an animal, human or the patient itself In all these cases, the configuration shown in FIG. 6 is a prothese ready for implantation into the patient. In case the graft vessel originates from the patient itself the prothese can be prepared well in advance of the ETS-anastomosis procedure or shortly before the actual ETS-anastomosis procedure while the patient is waiting on the operation table.

The configuration of FIG. 6 is obtained by inserting the graft 18 with its distal end stretched (not shown) through the ring member 15 and subsequently folding back the distal end of the graft vessel as is indicated with the arrows E. This folding back can be a complete folding back over 180° as is shown in the drawings with solid lines, but it can, within the scope of the claims, also be a partial folding back as is indicated in FIG. 6 with broken lines 31.

Referring to FIGS. 7a-7d, a ETS-anastomosis procedure with the laser catheter according to the invention will be described.

Figure 7A:
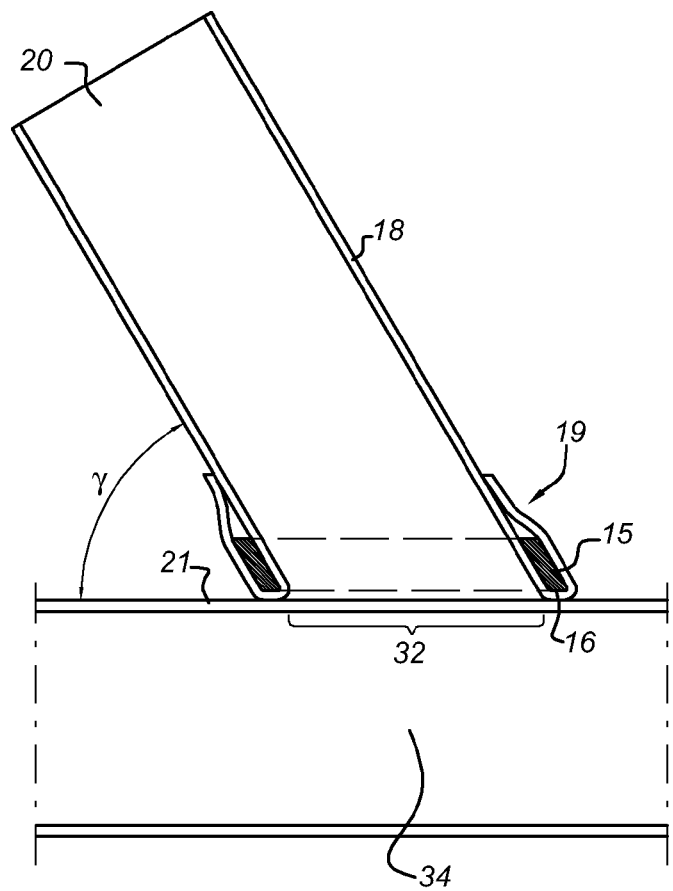

FIG. 7a shows a first step. The graft vessel 18 is attached to the side wall of the target vessel 21, leaving the part 32 of the wall tissue of the target vessel 21 in front of the lumen of the graft vessel 18 intact so that the blood flow in the target vessel 21 can be left undisturbed as there is no leakage possible. The graft vessel 18 can be fixed to the target vessel 21 by means—not shown—of suture wires, gluing, staples or an other connection technique know from the prior art, which does not require the part 32 of wall tissue to be removed before. The angle $\gamma$ will be about the same as the angle $\beta$ (see FIG. 4).

Figure 7B:
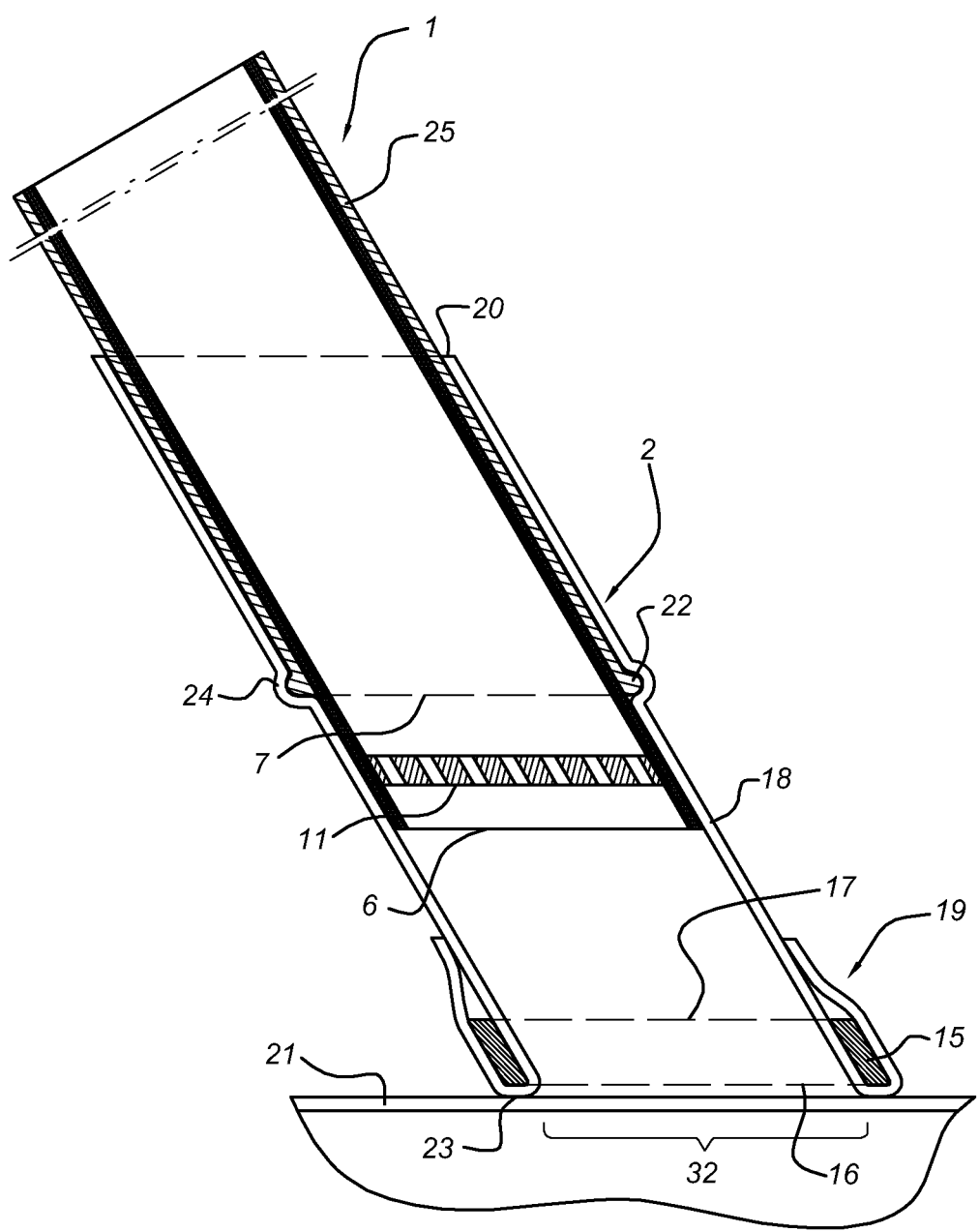
Figure 7C:
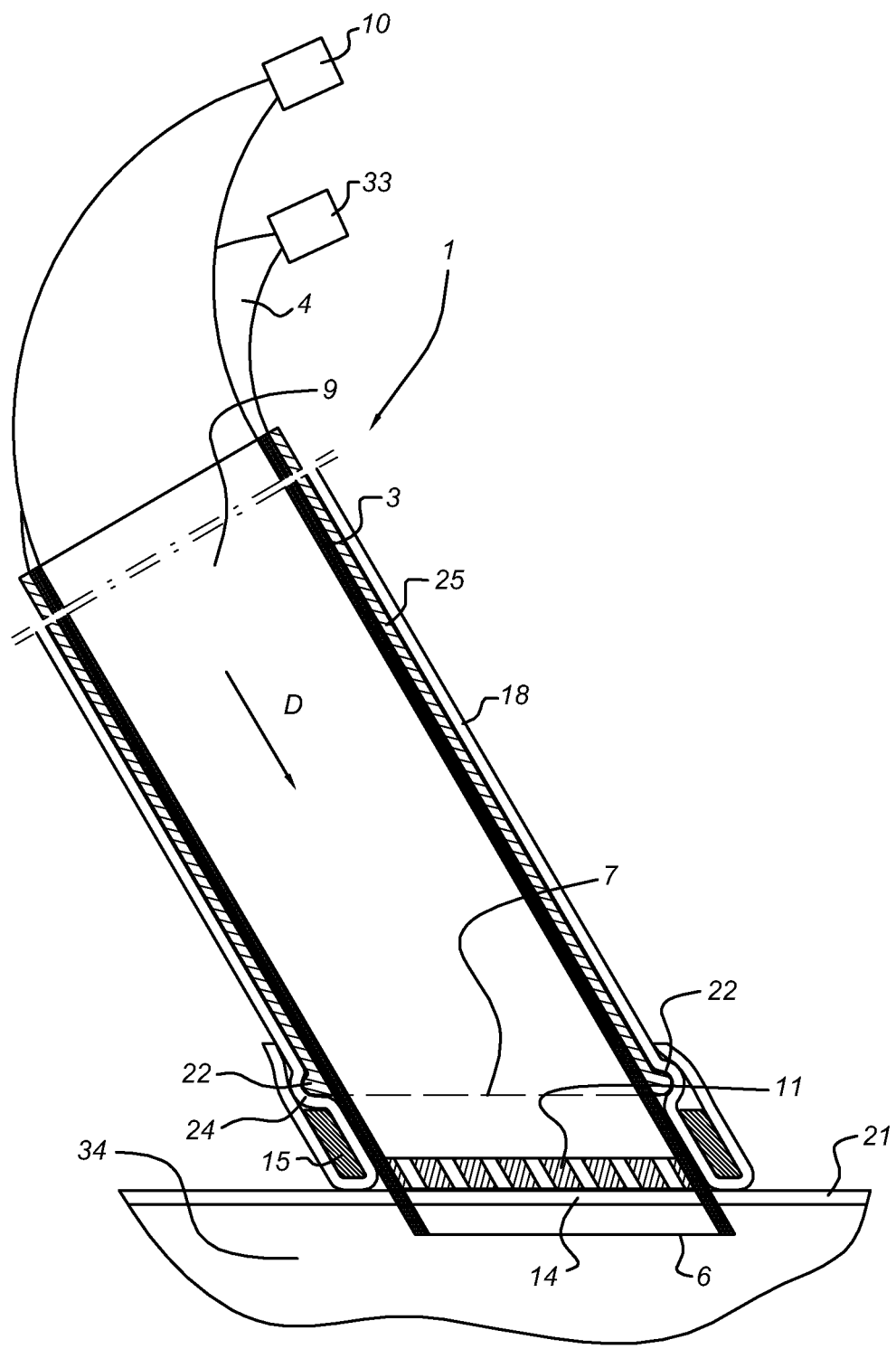

After a firm and sufficiently leak tight connection 23 between the graft vessel 18 and target vessel 21 has been established, the laser catheter of FIGS. 1-3 is inserted into the proximal end of the graft vessel 18, see FIG. 7b. As can be seen in FIG. 7b, the bulge 22 on the outer circumference of the laser catheter 1 causes a similar bulge 24 in the wall of the graft vessel. This bulge 24 allows the surgeon to see whether the light emergence surface 6 inside the graft vessel 18 is parallel to the wall part 32 to be removed from the target vessel and to control the correction of the position of the light emergence surface 6 by rotation of the catheter along its axis 8 in case it might not be parallel.

The laser catheter 1 is advanced distally (arrow D in FIG. 7b) up to the light emergence surface 6 contacts the wall part 32 to be removed from the target vessel. In case not already done before, the channel 9 and optical fibres 4 are, subsequently, connected to a vacuum source 10 and laser light source 33, respectively. A vacuum is applied to the channel 9 and the laser procedure is started. Laser light is emitted into the optical fibres 4. This laser light can be applied continuously or as a series of pulsations, for example during 5 seconds with a frequency of 40 Hz and an energy of about 10-25 mJ. Thus doing, the light emergence surface 6 gradually advances forward through the wall of the target vessel until said surface 6 faces or protrudes into the lumen 34 of the target vessel 21. The so called flap 14 is gripped by the suction mouth 11. At this moment, the laser procedure is finished and the laser light source can be switched off Subsequently, the laser catheter is retracted in the direction opposite to arrow D, whilst the flap 14 is being removed by the suction gripper 11.

As soon as the laser catheter has been retracted over a sufficient distance, a clip 26 (FIG. 7d) is placed on the graft vessel 18 in order to close it off Blood will be allowed to enter the graft vessel through the aperture 27, but will not be able to pass the clip 26. After removing the laser catheter completely, the proximal end 20 can be connected by a ETE-anastomosis (ETE=End To End) to another vessel, such as an other graft vessel, or it can be connected by an ETS-anastomosis to the same or another target vessel. The other graft or target vessel might be an artificial vessel or a natural vessel obtained from a donor.

Figure 7D:
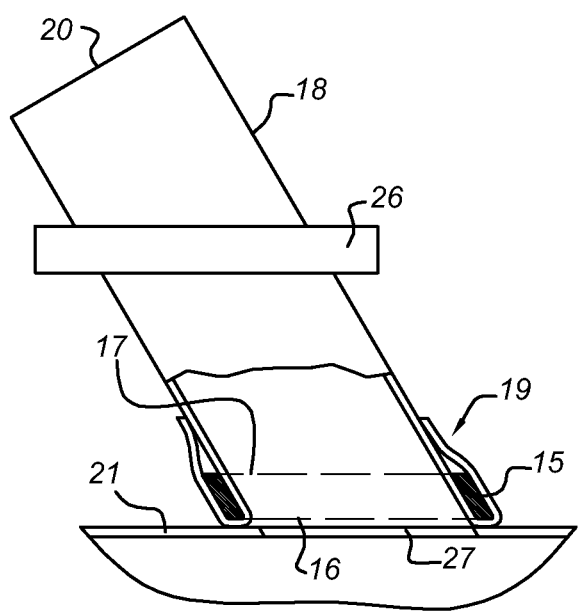
Figure 8:
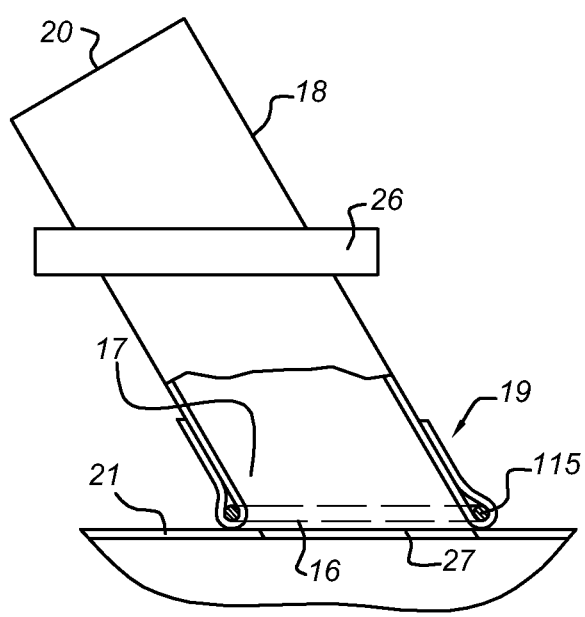
FIG. 8 shows an ETS anastomosis very similar to the one shown in FIG. 7d, the difference being essentially the design of the ring member.

FIG. 8 shows an ETS anastomosis, very similar to the one showed in FIG. 7d. The difference between FIG. 8 and FIG. 7d is the design of the ring member. In the embodiment according to FIG. 7d, the ring member 15 is so to say a short tube, whilst in the embodiment of FIG. 8, the ring member 115 is so to say a pure ring having an axial height which is smaller than or equal to the radial thickness of the wire from which the ring is made. The ring member 115 will have an oval shape (viewed in a plane parallel to the side wall of the target vessel). Taking into account this difference between FIGS. 8 and 7d, only the reference number for the ring member is taken differently, the other reference numbers, relating to the same parts, are the same. As will be clear, the embodiment with the ring member 115 also falls within the scope of the claims. Further, it will be clear that the ETS anastomosis of FIG. 8 can be made using the same procedure and laser catheter as shown in the FIGS. 1-7.

With respect to the ring member 15, 115, it is further noted that according to this invention, i.e. within the scope of the claims, this ring member might be provided with one or more protrusions, like anchoring pins, for penetrating through the wall of the graft vessel and/or target vessel.

The invention claimed is:

1. A laser catheter for bypass surgery, wherein the distal part of the catheter is provided with:
 a tubular arrangement of optical fibres, the fibre ends terminating with an angle having distal ends defining a ring-shaped light emergence surface for emitting a tubular bundle of light beams in the distal direction of the catheter,
 a stop surface extending around the tubular arrangement of optical fibres and facing in the distal direction, the stop surface being arranged at a distance proximally from the light emergence surface;
 wherein the light emergence surface slants at a slanting angle in the range of [20°, 60°] with respect to the longitudinal axis of the catheter.

2. The laser catheter according to claim 1, wherein said slanting angle is in the range of [40°, 50°].

3. The laser catheter according to claim 1, wherein, viewed in a cross-section transverse to the longitudinal axis of the catheter, the tubular arrangement of optical fibres has a circular cross section, and wherein, viewed perpendicular to the light emergence surface, the shape of the light emergence surface is elliptical.

4. The laser catheter according to claim 1, wherein the stop surface and light emergence surface are parallel to each other.

5. The laser catheter according to claim 1, wherein the distal part of the catheter is provided with a gripper for gripping tissue inside the tubular bundle of light beams.

6. The laser catheter according to claim 5, wherein the gripper comprises a hollow channel extending within the tubular arrangement of fibres and connectable to a vacuum source, the distal end of the channel defining a suction mouth.

7. The laser catheter according to claim 6, wherein the suction mouth is arranged at a distance proximally from the light emergence surface and defines a suction surface parallel to the light emergence surface.

8. The laser catheter according to claim 5, wherein the stop surface forms a radial bulge on the outer surface of the catheter.

9. The laser catheter according to claim 6, wherein the distal end of the channel is provided with a plate, defining the suction surface and provided with suction apertures.

10. An assembly for bypass surgery, comprising:
 a laser catheter according to claim 1; and
 a ring member having dimensions adapted for, on the one hand, insertion of the distal end of the tubular arrangement of optical fibres through said ring member and for, on the other hand, preventing passage of the stop surface through said ring member.

11. The assembly according to claim 10, wherein the ring member has an axial height which is at least 1 mm, wherein the ring member has two opposing axial end faces, and wherein the angle between at least one of said axial end faces and the axial direction of the ring member corresponds to said slanting angle.

12. The assembly according to claim 11, wherein the axial end faces of the ring member are mutually parallel.

13. The assembly for bypass surgery according to claim 10, further comprising a graft vessel having diameter dimensions allowing, on the one hand, passage of the laser catheter and, on the other hand, insertion through said ring member.

14. The assembly according to claim 13, wherein one end of the graft vessel is inserted through said ring member and folded over said ring member.

15. The laser catheter according to claim 1, wherein the distal ends of the optical fibres extend parallel to the longitudinal axis of the catheter.

* * * * *